(12) United States Patent
Jacob et al.

(10) Patent No.: US 8,466,678 B2
(45) Date of Patent: Jun. 18, 2013

(54) METHOD AND APPARATUS FOR ENHANCED IN VIVO MRI IMAGING

(75) Inventors: Richard E. Jacob, Kennewick, WA (US); Brett Amidan, Kennewick, WA (US); Kevin Minard, Kennewick, WA (US)

(73) Assignee: Battelle Memorial Institute, Richland, WA (US)

( * ) Notice: Subject to any disclaimer, the term of this patent is extended or adjusted under 35 U.S.C. 154(b) by 679 days.

(21) Appl. No.: 12/711,980

(22) Filed: Feb. 24, 2010

(65) Prior Publication Data
US 2010/0225316 A1    Sep. 9, 2010

Related U.S. Application Data

(60) Provisional application No. 61/155,225, filed on Feb. 25, 2009.

(51) Int. Cl.
*G01V 3/00*    (2006.01)

(52) U.S. Cl.
USPC ............................ 324/307; 324/309; 382/128

(58) Field of Classification Search
USPC .................................. 324/307, 309; 382/128
See application file for complete search history.

(56) References Cited

U.S. PATENT DOCUMENTS

| | | | |
|---|---|---|---|
| 6,477,399 B2 * | 11/2002 | Biswal et al. | 600/410 |
| 7,599,542 B2 * | 10/2009 | Brockway et al. | 382/132 |
| 7,901,873 B2 * | 3/2011 | Nicholson et al. | 435/4 |
| 8,265,359 B2 * | 9/2012 | Andrushkiw et al. | 382/128 |

* cited by examiner

*Primary Examiner* — Louis Arana
(74) *Attorney, Agent, or Firm* — Klarquist Sparkman, LLP

(57) ABSTRACT

A method and apparatus for detecting the presence of abnormal tissues of the present invention utilizing a magnetic resonance imaging system in communication with a computer. The apparatus is configured to define a confidence region using a probability based confidence interval calculation such as multivariate or bivariate analysis for at least two parameters in a normal tissue sample by making a magnetic resonance image, and then to evaluate a second sample by making a magnetic resonance image. Parameters detectable by magnetic resonance imaging 3 are selected from t1, t2, t2*, signal intensity, and diffusion.

22 Claims, 7 Drawing Sheets

METHOD AND APPARATUS FOR ENHANCED IN VIVO MRI IMAGING

CROSS-REFERENCE TO RELATED APPLICATIONS

This invention claims priority to Provisional Application Ser. No. 61/155,225 which was filed on Feb. 25, 2009.

TECHNICAL FIELD

This invention relates to magnetic resonance imaging (MRI). More specifically, this invention relates to improved techniques for distinguishing healthy tissues from diseased or injured tissues using MRI.

BACKGROUND OF THE INVENTION

For more than 20 years, researchers have been attempting to apply magnetic resonance imaging (MRI) to the characterization and diagnosis of pulmonary diseases. In part, this is motivated by the ongoing need for non-invasive methods to diagnose and stage interstitial diseases that challenge clinicians. Of particular interest in pulmonary MRI research is the potential to distinguish inflammation from fibrosis regionally and non-invasively. Although this is important for diagnosis and characterization of disease and disease activity, emphasis is often placed on assessing and differentiating patients for appropriate courses of treatment.

The most routinely used modality for thoracic imaging is x-ray computed tomography (CT); however, CT lacks specificity in some situations. This lack of specificity is described in the following publications:

Yi C A, Lee K S, Han J, Chung M P, Chung M J, Shin K M. 3-T MRI for differentiating inflammation- and fibrosis-predominant lesions of usual and nonspecific interstitial pneumonia: comparison study with pathologic correlation. AJR Am J Roentgenol 2008; 190(4): 878-885.

American Thoracic Society/European Respiratory Society International Multidisciplinary Consensus Classification of the Idiopathic Interstitial Pneumonias. This joint statement of the American Thoracic Society (ATS), and the European Respiratory Society (ERS) was adopted by the ATS board of directors, June 2001 and by the ERS Executive Committee, June 2001. Am J Respir Crit Care Med 2002; 165(2):277-304.

Lutterbey G, Grohe C, Gieseke J, et al. Initial experience with lung-MRI at 3.0 T: Comparison with CT and clinical data in the evaluation of interstitial lung disease activity. Eur J Radiol 2007; 61(2):256-261.

Jung J I, Park S H, Lee J M, Hahn S T, Kim K A. MR characteristics of progressive massive fibrosis. J Thorac Imaging 2000; 15(2):144-150.

Because MRI is able to distinguish tissue types, it is a promising imaging modality for disease diagnosis. To date, there have been several studies focused on characterizing and differentiating inflammation and fibrosis using various MRI techniques, such as T1-weighted imaging, T2-weighted imaging, and signal intensity (S0) changes with contrast agent wash-in or wash-out. These studies are described in the following papers:

McFadden R G, Carr T J, Wood T E. Proton magnetic resonance imaging to stage activity of interstitial lung disease. Chest 1987; 92(1):31-39.

Berthezene Y, Vexler V, Kuwatsuru R, et al. Differentiation of alveolitis and pulmonary fibrosis with a macromolecular MR imaging contrast agent. Radiology 1992; 185(1):97-103.

Kersjes W, Hildebrandt G, Cagil H, Schunk K, von Zitzewitz H, Schild H. Differentiation of alveolitis and pulmonary fibrosis in rabbits with magnetic resonance imaging after intrabronchial administration of bleomycin. Invest Radiol 1999; 34(1):13-21.

Yi C A, Lee K S, Han J, Chung M P, Chung M J, Shin K M. 3-T MRI for differentiating inflammation- and fibrosis-predominant lesions of usual and nonspecific interstitial pneumonia: comparison study with pathologic correlation. AJR Am J Roentgenol 2008; 190(4): 878-885.

Jung J I, Park S H, Lee J M, Hahn S T, Kim K A. MR characteristics of progressive massive fibrosis. J Thorac Imaging 2000; 15(2):144-150.

Bottomley P A, Hardy C J, Argersinger R E, Allenmoore G. A Review of H-1 Nuclear-Magnetic-Resonance Relaxation in Pathology—Are T1 and T2 Diagnostic. Medical Physics 1987; 14(1):1-37.

Karmouty-Quintana H, Cannet C, Zurbruegg S, et al. Bleomycin-induced lung injury assessed noninvasively and in spontaneously breathing rats by proton MRI. J Magn Reson Imaging 2007; 26(4):941-949.

Others have used non-imaging techniques to measure T1, T2, or water diffusion in excised lungs. These studies are described in the following papers:

Cutillo A G, Chan P H, Ailion D C, et al. Characterization of bleomycin lung injury by nuclear magnetic resonance: correlation between NMR relaxation times and lung water and collagen content. Magn Reson Med 2002; 47(2):246-256.

Taylor C R, Sostman H D, Gore J C, Smith G W. Proton relaxation times in bleomycin-induced lung injury. Invest Radiol 1987; 22(8):621-626.

Generally, measurements of T1 and water diffusion have not shown any ability to distinguish inflammation and fibrosis, and measurements of T2 have had mixed results. In the latter case, Taylor et al. reported an increase in T2 with chronic fibrosis and a decrease with inflammation in bleomycin-dosed mice, opposite that in bleomycin-dosed rats reported by Cutillo et al. Results of S0 measurements also show that signal intensity may help distinguish inflammation and fibrosis. However, results were generally based on prior knowledge of dose history or disease state, and the ability to blindly distinguish between inflammation, fibrosis, and admixtures of the two was not demonstrated. There are even conflicting reports of S0 changes. For example, Kersjes et al. showed a significant increase in S0 only three hours after bleomycin exposure in rabbits, while Karmouty-Quintana et al. showed no increase in S0 even after 24 hours in a similar experiment with rats. Although some variation in reported results may be attributed to species-specific differences in bleomycin reactions, the apparent lack of a single parameter or set of parameters that can reliably identify inflammation and fibrosis warrants further investigation.

Accordingly, there exists a need for new methods and techniques that offer improvements over the prior art. The present invention fulfills that need.

SUMMARY OF THE INVENTION

The present invention uses magnetic resonance imaging for medical and diagnostic purposes to detect the presence of abnormal tissues. The present invention improves upon prior art methods of using magnetic resonance imaging because the present invention is able to distinguish between tissues that are indistinguishable using prior art methods.

As shown in FIG. 1, the apparatus for detecting the presence of abnormal tissues of the present invention utilizes a magnetic resonance imaging system 1 in communication with a computer 2. The apparatus is configured to detect at least two parameters at a set of data points in at least one first tissue sample by making a magnetic resonance image of at least one first tissue sample. The apparatus is further configured to then detect at least two parameters at a set of data points in a second tissue sample by making a magnetic resonance image of a second tissue sample. The apparatus is further configured to then generate a set of measured data points for each tissue sample for each of the selected parameters. The apparatus is further configured to calculate a confidence region using the measured data points from at least one first tissue sample. Finally, the apparatus is further configured to identify data points from at least one second tissue sample that do not fall within the calculated confidence region.

The method of the present invention is shown in FIG. 2. The method begins with step of selecting at least two parameters detectable by magnetic resonance imaging 3. Using a magnetic resonance imaging system, the method then generates a first set of measured data points from at least one baseline tissue by measuring the selected parameters at a first set of data points in the baseline tissue 4. The method then determines a confidence region using the measured data points 5. The method then uses magnetic resonance imaging to generate a second set of measured data points from a second tissue by measuring the selected parameters at a second set of data points in the second tissue sample 6. The method then identifies the data points from the second set of measured data points that do not fall within the confidence region 7.

Preferably, but not meant to be limiting, the parameters detectable by magnetic resonance imaging 3 are selected from t1, t2, t2*, signal intensity, diffusion, and combinations thereof. More preferably, but also not meant to be limiting, the parameters detectable by magnetic resonance imaging 3 are t2 and signal intensity.

As used herein, the term "T1" is defined to mean the spin-lattice relaxation time constant, which characterizes the time of signal regrowth (the time required for spins to align with the magnetic field). As used herein, the term "T2" is defined to mean the spin-spin relaxation time constant, which characterizes the signal decay after an RF pulse is applied due to dephasing of transverse magnetization. As used herein, the term "T2*" (pronounced "Tee Two Star") is defined to mean the relaxation time constant of transverse magnetization caused by magnetic field inhomogeneties. As used herein, the term "Signal Intensity" is defined to mean the strength or magnitude of the MR-measured signal. As used herein, the term "Diffusivity" is defined as a number that describes the inherent mobility, or Brownian motion, of an atom or molecule.

When performing the step of using a magnetic resonance imaging system, the method generates a first set of measured data points from at least one baseline tissue by measuring the selected parameters at a first set of data points in the baseline tissue 4. The measured data points can be taken from only one baseline tissue, or they can be taken from several baseline tissues. While not meant to be limiting, measured data points taken from several baseline tissues may be combined, for example by averaging the data using simple or weighted averaging techniques, or otherwise manipulated to generate a composite first set of data points that represents a baseline tissue. Those having ordinary skill in the art will recognize that it is preferred that the baseline tissues be selected as tissues that do not have the anomaly that is suspected in the second tissue sample. Thus, by way of example and not meant to be limiting, when the second tissue sample is a lung suspected of having cancerous growths, it is preferred that baseline tissue or baseline tissues used to generate a composite first set of data points be healthy, non-cancerous tissues.

When determining a confidence region using the measured data points 5, the present invention can use any of a variety of mathematical tools that will readily recognized by those having ordinary skill in the art as providing a suitable confidence region as output. For example, and not meant to be limiting, the step of generating the confidence region is preferably performed by using a probability based confidence interval calculation, and is more preferably performed using a multivariate analysis. In embodiments using just two selected parameters at the first and second set of data points, it is preferred that the step of generating the confidence region is preferably performed by using a bivariate analysis.

Those having ordinary skill in the art will recognize that the process of making a magnetic resonance image will often result in an image that encompasses a larger portion of the tissue than the region of interest for medical and diagnostic purposes. Accordingly, it is preferred, although not meant to be limiting, that the measurements of the selected parameters from portions of the magnetic resonance image that lie outside of the first set of data points are ignored during the step of generating the confidence region. Likewise, it is also preferred, although not meant to be limiting, that the measurements of the selected parameters from portions of the magnetic resonance image that lie outside of the second set of data points are also ignored during the step of identifying the data points from the second set of measured data points that do not fall within the confidence region 7.

To assist one using the present invention in realizing the full benefits of the present invention, the invention preferably performs the additional step of highlighting the data points from the second set of measured data points that do not fall within the confidence region onto their location in an image of the second tissue. In this manner, the practitioner can readily identify the exact location of any abnormalities. Those having ordinary skill in the art will recognize that this step can be performed by a variety of different approaches. Preferred among these approaches is the generation of an image of the second tissue wherein the image delineates the location of the data points from the second set of measured data points that do not fall within the confidence region.

BRIEF DESCRIPTION OF THE DRAWINGS

The following detailed description of the embodiments of the invention will be more readily understood when taken in conjunction with the following drawing, wherein.

The Figure: An illustration of the apparatus of the present invention.

t8=1050 μs. The dashed lines indicate the CPMG loop. Note that t7 and t8 exceed P1 and P2, respectively, to allow for gradient stabilization.

Figure 4A:
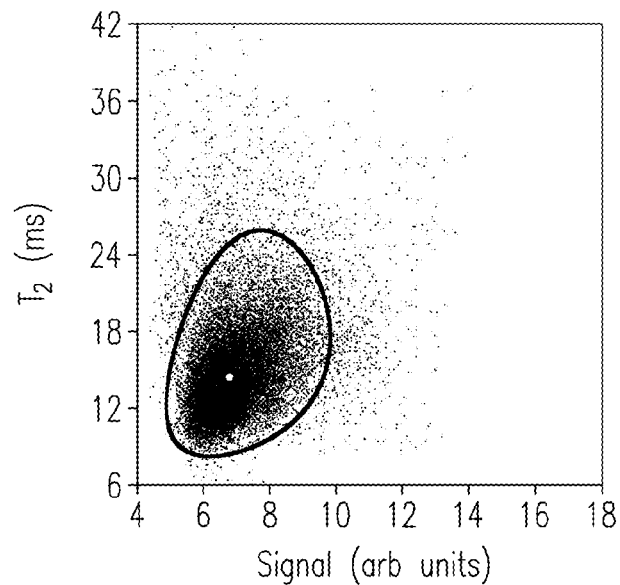
Figure 4B:
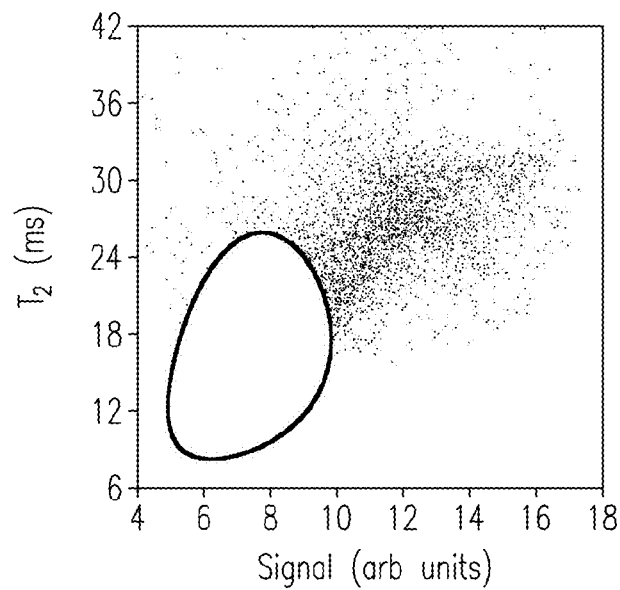

FIG. 4A is a graph showing data from control rats at week 2. The ellipsoid shown defines the 95% confidence region of "normal" tissue. Each data point in the plot represents a single pixel from the segmented lung images. The white dot indicates the median value of T2 and S0. Figure 4B is a graph showing representative data from a HD rat at week 2. The same ellipsoid is shown, and "normal" data points have been deleted.

Figure 5:

FIG. 5 is a single slice from a representative HD rat (same as that shown in FIG. 3B) at the five different time-points. Proton images (grayscale) are superposed with maps of "abnormal" pixels (grayscale).

FIG. 6 is an example of the histological analysis of collagen content. A) Mosaic of histological images of a coronal slice from the left lung of a HD rat. The lung was stained with a tri-chrome stain to highlight the collagen as blue. B) Filtered binary image showing tissue. C) Filtered binary image showing only blue-stained tissue.

Figure 7:
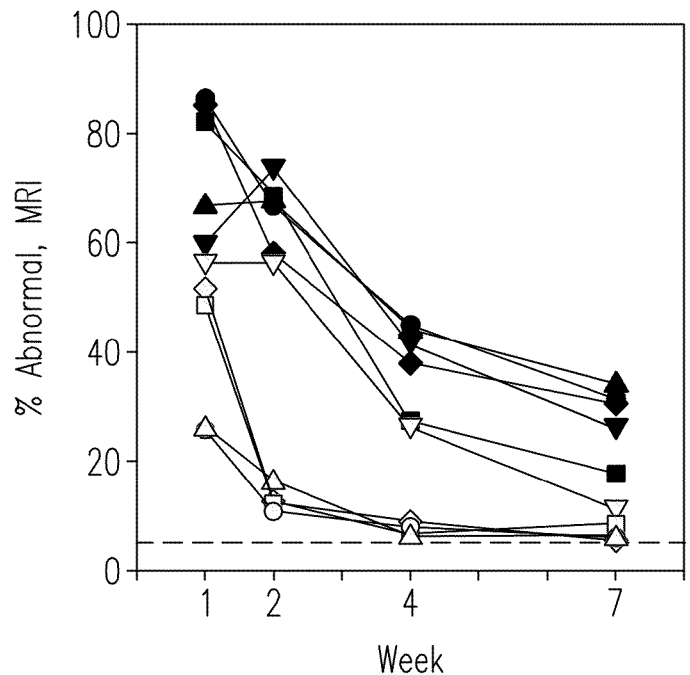

FIG. 7 is a graph showing the percentage of pixels found to be "abnormal" (i.e. outside the 95% confidence ellipsoid, as illustrated in FIG. 4) for each dosed animal at each time point. Control animals are 5% "abnormal" by definition and are represented by the dashed line. The solid shapes represent individual HD rats, and the open shapes represent LD rats.

Figure 8:
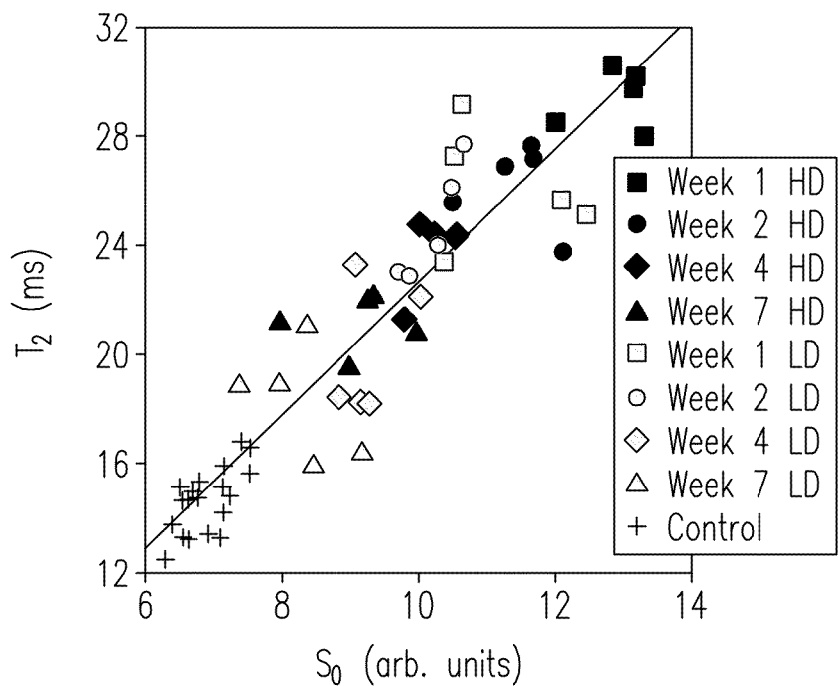

FIG. 8 is a graph showing the average of the "abnormal" data from low dose (LD) and high dose (HD) rats, and average of all data from control rats, at all time points. The line represents a least-squares linear fit through all the data, with a correlation or r=0.93 and p<0.001.

Figure 9:
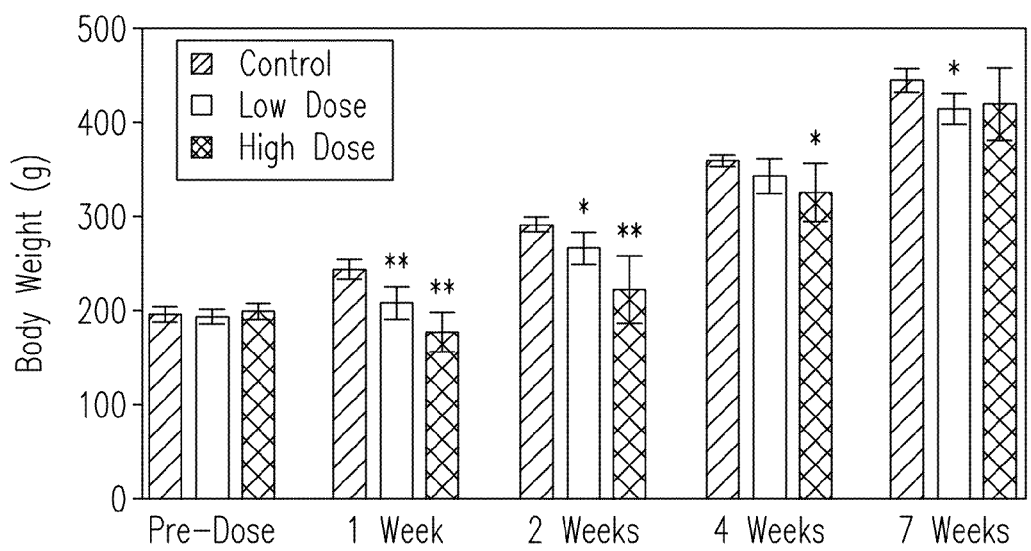
Figure 10A:
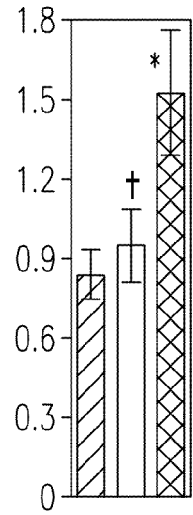
Figure 10B:
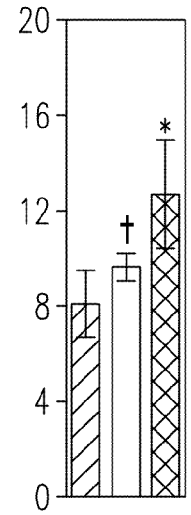
Figure 10C:
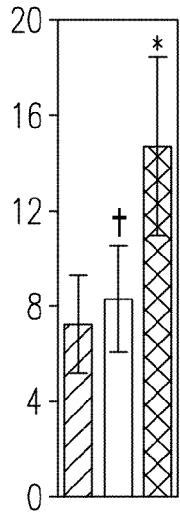
Figure 10D:
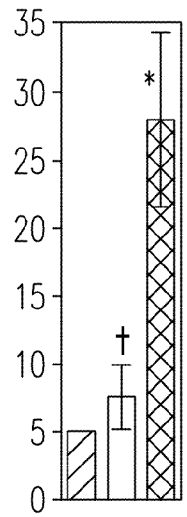
Figure 10E:
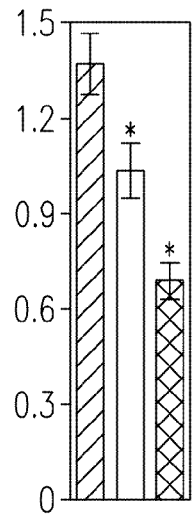

FIG. 9 is a graph showing the mean body weights of the three dose groups at all time points, a general indication of animal welfare. Significance from control group is shown by: *p<0.05 and **p<0.005. Error bars represent the standard deviation.

FIG. 10 is a graph showing the data means taken at week 7 for each dose group showing: A) Water content of the right lungs measured gravimetrically, in grams; B) Collagen content of the right lungs measured by the hydroxyproline method, in percentage of the total dry lung weight; C) Collagen content of the left lungs as measured by histology, in percentage of the total number of tissue pixels; D) Pixels determined to be "abnormal" by MRI, in percentage of the total number of lung pixels; and E) In vivo quasistatic chord compliance measured in a bench top pulmonary function test system, in mL/cmH2O. Error bars represent standard deviations (control animals measured by MRI are 5% "abnormal" by definition and thus have no error bars). *p<0.005; †p≧0.05

DETAILED DESCRIPTION OF THE PREFERRED EMBODIMENTS

For the purposes of promoting an understanding of the principles of the invention, reference will now be made to the embodiments illustrated in the drawings and specific language will be used to describe the same. It will nevertheless be understood that no limitations of the inventive scope is thereby intended, as the scope of this invention should be evaluated with reference to the claims appended hereto. Alterations and further modifications in the illustrated devices, and such further applications of the principles of the invention as illustrated herein are contemplated as would normally occur to one skilled in the art to which the invention relates.

To demonstrate the present invention, a series of experiments were conducted to investigate the ability of the present invention to use proton (1H) magnetic resonance imaging (MRI) to distinguish between pulmonary inflammation and fibrosis. In these experiments, three groups of Sprague-Dawley rats (n=5) were instilled intratracheally with bleomycin (2.5 U/kg or 3.5 U/kg) in saline or with saline only. Rats were imaged at 2.0 T using a multi-slice Carr-Purcell-Meilboom-Gill (CPMG) sequence with 6 ms echo spacing. Signal intensity (S0) and T2 were calculated on a pixel-by-pixel basis using images collected before dosing and 1, 2, 4, and 7 weeks after. At each time point, data from dosed animals were compared to controls, and bivariate statistical analysis was employed to classify image pixels containing abnormal tissue. At week 7, pulmonary function tests were performed, then all rats were sacrificed, left lungs were formalin fixed and tri-chrome stained for histological analysis of collagen content, and right lungs were used to measure water and hydroxyproline (collagen) content. The product S0×T2 significantly correlated with water and collagen content in the high-dose group (p=0.004 and p=0.03, respectively). These experiments thus demonstrated that the present invention can utilize MRI to confidently localize pulmonary inflammation and fibrosis.

While the purpose of this particular study was to examine the potential utility of using altered S0 and T2 relaxation to distinguish pulmonary inflammation and fibrosis, those having ordinary skill in the art will recognize that the techniques described herein will have general applicability to any interrogation using MRI, and particular advantages when performing in vivo interrogation. Since the instillation of bleomycin in the lungs of live rats is a well-characterized and accepted model for human disease, it was used in this study. The study measured both T2 and S0, then determined the location of abnormal tissue using a bivariate normal confidence interval with the hypothesis that multivariate analysis would improve specificity.

Animal handling and treatment procedures followed a protocol approved by the Institutional Animal Care and Use Committee. A total of 18 male Sprague-Dawley rats weighing 196±8 g were used. They were divided into three groups of n=6: control, low-dose (LD), and high-dose (HD). A single animal per dose group died immediately after dosing. Therefore, each group was left with n=5. No additional unanticipated mortality occurred for the duration of the experiment.

Rats were imaged at 5 time points: pre-dose, then 1, 2, 4, and 7 weeks post-dose. Animals were prepared for imaging as described in Jacob R E, Minard K R, Laicher G, Timchalk C. 3D 3He diffusion MRI as a local in vivo morphometric tool to evaluate emphysematous rat lungs. J Appl Physiol 2008; 105 (4):1291-1300.

In brief, rats were first weighed then injected subcutaneously with 0.02 mL/kg body weight (BW) glycopyrrolate to inhibit oral secretions and facilitate insertion of an endotracheal tube. After 10-15 minutes, animals were anesthetized with 3-4% isoflurane in oxygen-enriched air (30% O2, 70% N2). HD rats were found to struggle with breathing under anesthesia and were therefore ventilated with pure O2 at weeks 1, 2, and 4; O2 content is not expected to significantly affect T2 measurements, particularly when measured with a Carr-Purcell-Meilboom-Gill (CPMG) sequence.

Rats were intubated with a 14-gauge catheter tube and connected to an MR-compatible mechanical ventilator that continued to deliver isoflurane. The breathing rate was set to 54.5 breaths per minute (1.1 seconds per breath). A maximum inflation pressure of 12±2 cmH2O was reached in 220 ms, followed by a passive exhalation period of 320 ms. A breath hold was then maintained for 550 ms during which MRI data accumulation took place. The ventilator provided a gating signal 88 ms after the start of each breath hold. Pulse rate and body temperature were monitored (SA Instruments, Stony Brook, N.Y., model 1025). Warm air (40-50° C.) was circulated within the magnet bore to maintain body temperature at 36±2° C.

Figure 3:
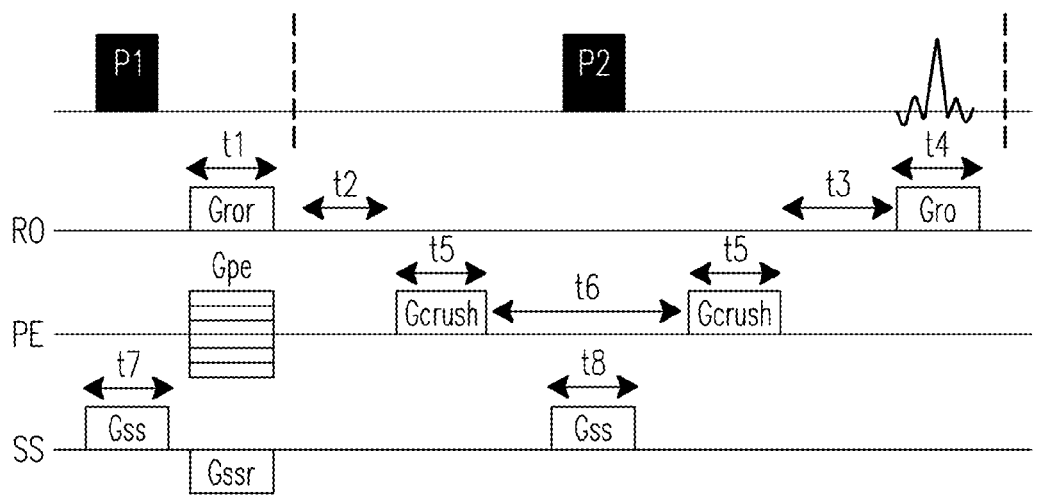
FIG. 3 is a schematic of the MRI pulse sequence used in the experiments that demonstrated a preferred embodiment of the present invention. RF pulses: P1=750 µs, 90°; P2=750 µs, 180°. Gradients: read-out refocus Gror=3.75 G/cm; read-out Gro=2.35 G/cm; phase-encode Gpe ranged from ±2.605 G/cm in steps of 0.0407 G/cm; spoiler gradients Gcrush=1.5 G/cm; slice selection Gss=5.56 G/cm; slice selection refocus Gssr=−4.91 G/cm. Sequence timing: t1=450 µs; t2=280 µs, t3=330 µs; t4=1.33 ms; t5=1.4 ms; t6=1090 µs; t7=850 µs.

Imaging was performed using a 2.0 T horizontal-bore magnet (Oxford, UK) equipped with 150 mT/m gradients (Resonance Research, Billerica, Mass.) and a Varian UnityPlus console (Palo Alto, Calif.). The bore diameter with gradients in place was 12 cm. A home-built, 8-leg birdcage coil 15 cm long and 7 cm inner diameter was tuned to the 1H frequency (84.9 MHz). A small tube of water doped with a Gd-based contrast agent was placed next to the animal to act as a signal calibration phantom. Eight T2-weighted images were acquired with an eight-echo, slice selective CPMG imaging sequence with a 6 ms echo spacing as described in Bernstein M A, King K F, Zhou X J. Handbook of MRI Pulse Sequences. San Diego, Calif.: Elsevier Academic Press; 2004. Pulse sequence details are shown in FIG. 3.

The MRI scanner was triggered by the ventilator on every breath, therefore the repetition time TR=1.1 s. Five coronal slices, 2.5 mm thick and separated by 0.5 mm, were acquired covering most of the lung, particularly regions dorsal to the heart. Therefore, a total of 40 images were obtained for each animal at each time point. The acquisition bandwidth was 96 kHz, and the field of view was 9.6 cm×12.8 cm. With a total of 128×128 points, images had a planar resolution of 0.75 mm (lateral axis)×1.0 mm (anteroposterior axis). Four signal averages were used to minimize effects of cardiac motion. Total imaging time was 9.4 min, plus 10-15 min of set-up time for coil tuning, animal positioning, and slice selection. One control rat was not imaged at week 2 due to technical problems.

After the initial MR imaging session, rats were maintained supine on the ventilator and were slowly revived from anesthesia until breathing on their own but still unconscious. Animals were disconnected from the ventilator, and a mixture of 0.2 mL saline (0.9% sodium chloride) and either 2.5 U/kg BW (LD) or 3.5 U/kg BW (HD) of bleomycin sulfate (Calbiochem, La Jolla, Calif.) was instilled through the trachea tube; control animals received saline only. With this model, it is widely reported that acute lung inflammation peaks about 1 week following intratracheal bleomycin administration, then chronic fibrosis begins to appear within 2-4 weeks. After dosing, animals were temporarily reattached to the ventilator to assist in breathing, if necessary.

The LD group showed a very mild response after the first two weeks of the study. The reason why is not clear, although the bleomycin activity can range from 1.5-2.0 U/mg, according to the vendor (Calbiochem). Therefore, new bleomycin and additional age-matched animals were ordered; this second group received 3.5 U/kg BW and became the HD cohort.

MRI Analysis. Images were reconstructed using a standard 2D Fourier transform, then they were read into Mathematica 6.0 (Wolfgram Research, Champaign, Ill.) for further analysis. Images of each rat at each time point were sorted into 5 data stacks—one stack for each slice—each composed of the 8 T2-weighted images. The mean background noise was measured from the first image of each stack. Image stacks were then thresholded to eliminate pixels whose signal intensity was <10× the noise level (typical signal-to-noise ratio of healthy lung was ≈20). Using the NonLinearRegress function of Mathematica, remaining pixels were fit to:

$$S = S_0 \exp(-t/T_2)$$

where S is the signal intensity of each image, S0 is the initial signal intensity, t is the echo time, and T2 is the spin-spin relaxation time. The background noise was taken into consideration in the fit using the standard root-sum-squares method. The parameters S0 and T2 were extracted from the fit, and pixels whose standard error (fit uncertainty) exceeded 50% were discarded. S0 and T2 maps were then generated for each image slice. Multi-exponential behavior of water T2 relaxation in lungs and in collagen has been well documented, with T2 values of order 10 ms, 50 ms, and 300 ms representing different fractions of the total MR signal. In this work, T2 was measured out to 48 ms in 6 ms intervals; over this time scale no multi-exponential behavior was observed. The first slice of each stack had ~30% higher S0 than the following slices due to rf bleed-through from an imperfect slice profile. Thus, the first slice, which generally contained more heart than lung, was discarded from analysis.

As observed in previous experiments, the breath hold pressure varied from animal to animal. This is because each rat was allowed the same fixed exhale duration, and compliance variations due do to differences in animal size and depth of anesthesia likely resulted in different rates of exhalation. S0 correlated strongly with the breath hold pressure for untreated and control rats (r=0.94, p<0.0001), therefore a linear correction was applied to normalize the S0 data of all animals to facilitate direct comparisons between animals. T2 did not correlate with breath hold.

To exclude non-lung tissue from further analyses, ImageJ (Rasband W S. ImageJ: U.S. National Institutes of Health, Bethesda, Md., USA, http://rsb.info.nih.gov/ij/; 1997-2009) was used to manually segment the lungs in the S0 and T2 maps. It was inevitable for some surrounding tissue and vasculature to be included in the segmentation, as it was difficult to clearly discern the lung boundary in some cases, particularly in dosed animals.

Figure 1:
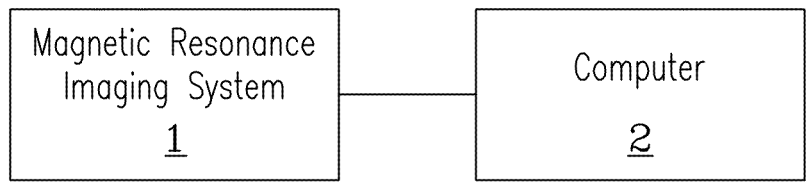
FIG. 1 is a schematic representation of an apparatus disclosed herein.
Figure 2:
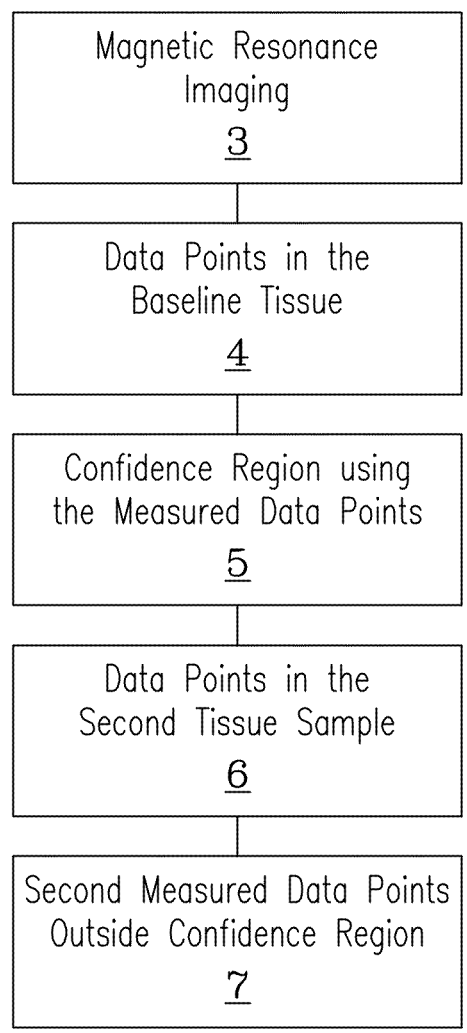
FIG. 2 is a schematic representation of a method disclosed herein.

Following segmentation, data for each rat at each time point were written to a columnar data file that contained S0, T2, slice number, and the corresponding pixel coordinates. For each time point, data from control rats were combined into a single data set. A scatter plot of T2 (y-axis) vs. S0 (x-axis) was then generated to show the clustering of the data and the relationship between the measured parameters (for example, see FIG. 2A). Using a Mathematica script and bivariate statistical analysis, an ellipsoid was calculated that encircled ~95% of the data points that were heretofore defined as "normal" lung with 95% confidence.

Each dosed animal was compared to the control group at the same time point, and data points within the ellipsoid were deleted as shown in FIG. 4B. The percentage of total pixels that were "abnormal" was calculated for each animal at each time point. For control rats, this percentage was 5% by definition.

Each "abnormal" data point retained its original image coordinates, which facilitated the creation of a "disease map", or a map showing pixels that had a high probability (≥95%) of not representing normal lung tissue. These maps were then superposed on the original MR images to show disease location. FIG. 5 shows an example of this for an HD rat at all time points.

Pulmonary Function Tests: Several hours after the final imaging session (at week 7), animals were subjected to pulmonary function tests using a Buxco Forced Maneuvers system (Buxco Research Systems, Wilmington, N.C.). Animals were anesthetized with an intraperitoneal injection of 87% ketamine/13% xylazine at a dose of 2 mL/kg BW. A trachea tube was then surgically inserted, and the animals were placed supine into the plethysmograph. Static lung volumes, fast flow volumes, and quasistatic chord compliance (QCC) were measured (25); however an error that occurred during data collection resulted in only the QCC measurements being recorded. A pressure-volume (PV) curve was recorded during a controlled exhale from 30 cmH2O to −20 cmH2O; QCC results reported herein were taken from the pressure range of 2-8 cmH2O, within the linear region of the PV curves.

Post-Mortem Chemical and Histological Analysis: Immediately following the pulmonary function tests, rats were sacrificed by CO2 asphyxiation, the lungs were harvested, and right and left lungs were separated. To gravimetrically determine water content, the right lungs were weighed, inflated with air and dried overnight, then weighed again.

After being dried and weighed, the right lungs were used to measure collagen content by analysis of hydroxyproline (Hyp), closely following the method published by Reddy et al. (Reddy G K, Enwemeka C S. A simplified method for the analysis of hydroxyproline in biological tissues. Clin Biochem 1996; 29(3):225-229). The tracheas were removed from the dried right lungs, then the lungs were homogenized. Hyp concentrations were measured in three ~25 mg samples of each lung. The amount of collagen in the lungs (in mg per gram of dry lung) was calculated by multiplying the Hyp concentrations by 7.7, then the percentage of dry lung that was collagen by weight was calculated.

Figure 6A:
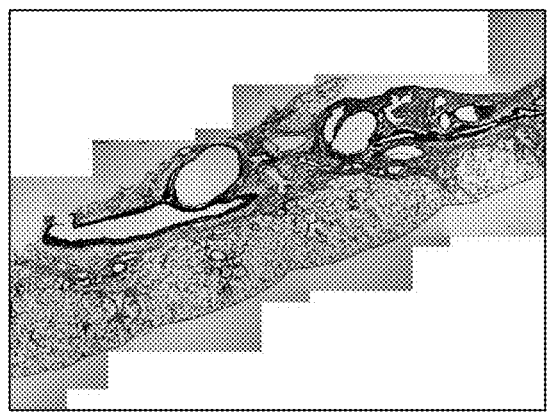
Figure 6B:
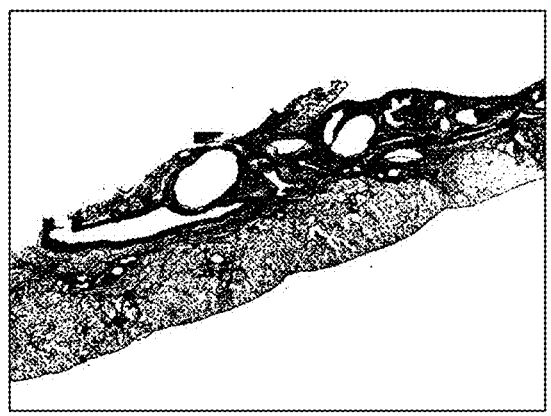
Figure 6C:
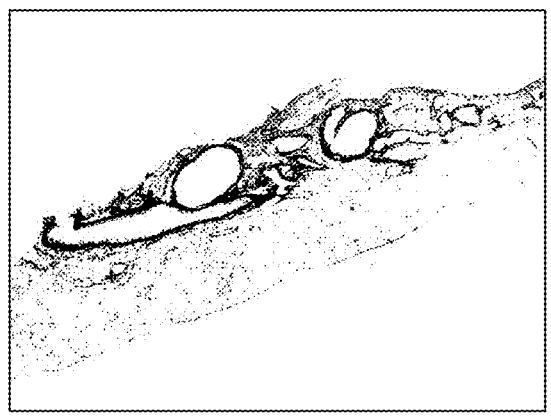

Immediately after harvest, the left lungs were inflated with formalin (10% formaldehyde) to a pressure of ≈25 cmH2O, then were tied off and placed in a formalin bath for >48 hours. They were then sectioned, embedded with paraffin, and stained with a trichrome stain to label the collagen blue. Several (5 or 6 per lung) roughly coronal 5 μm thick slices were prepared for microscopic visualization. Color digital photographs were taken of all slices at 20× magnification. Next, a Mathematica script was used to determine the percentage of tissue that was collagen based on empirically determined RGB color filters. The same filter settings were used for all images. FIG. 6 shows an example of the histological analysis performed on a tissue section of a HD rat. FIG. 6A shows the original microscope images formed into a mosaic, FIG. 6B shows the results of the tissue filter (i.e. with background eliminated), and FIG. 6C shows the results of the blue filter. Coronal histological slices were taken to facilitate potential comparison of disease location in histological samples with the coronal MR image slices. However, this was confounded by changes to the lung shape due to removal from the chest cavity and the sectioning process; therefore comparisons were not possible.

Statistics: Bivariate normal confidence interval formulas were used to create the 95% confidence ellipsoids from control data, as shown in FIG. 4A. In order to better assume a normal distribution of the data, a log transformation was first performed. Next, the 2×2 variance-covariance matrix was calculated using the equation A.1:

$$VCM = \begin{vmatrix} var[\ln(S_0)] & \dfrac{\sum_m \ln(S_0) + \sum_m \ln(T_2)}{m} - \\ & \overline{\ln(S_0)} \times \overline{\ln(T_2)} \\ \dfrac{\sum_m \ln(S_0) + \sum_m \ln(T_2)}{m} - & var[\ln(T_2)] \\ \overline{\ln(S_0)} \times \overline{\ln(T_2)} & \end{vmatrix} \quad \text{A.1}$$

where the bar indicates the mean value, var[z] is the variance, and m is the total number of data points. A log transformation was used to generate a normal distribution, as indicated in Eq. A.1. Next, an ellipsoid "radius" r was calculated assuming an F-distribution $F_{n,m}(x)$ is equation A.2:

$$F_{n,m}(x) = I\left(\dfrac{nx}{m+nx}; \dfrac{1}{2}n; \dfrac{1}{2}m\right) \tag{A.2}$$

$$r = \sqrt{2 \times F_{n,m}(x)} \tag{A.3}$$

where I(x;a,b) is the regularized beta function, n is the numerator degrees of freedom (number of independent variables), and m is the denominator degrees of freedom (number of data points minus 1). The built-in Mathematica 6.0 function that calculates the F-distribution with a given confidence level C (where $0 \leq C \leq 1$) is: Quantile[FRatioDistribution[n, m],C]. For the 95% confidence interval calculated herein, C=0.95.

$$CD = \begin{bmatrix} \sqrt{VCM_{11}} & \dfrac{VCM_{12}}{\sqrt{VCM_{11}}} \\ 0 & \sqrt{VCM_{22} - \left(\dfrac{VCM_{12}}{\sqrt{VCM_{11}}}\right)^2} \end{bmatrix} \tag{A.3}$$

Following this, the Cholesky decomposition was calculated as a 2×2 matrix as shown in equation A.3. Finally, x and y coordinates defining the perimeter of the ellipsoid were calculated.

$$x = \exp[\overline{\ln(S_0)} + r \times (\cos\theta \times CD_{11} + \sin\theta \times CD_{21})]$$

$$y = \exp[\overline{\ln(T_2)} + r \times (\cos\theta \times CD_{12} + \sin\theta \times CD_{22})] \tag{A.4}$$

A discrete number of angles q can be chosen to describe the ellipsoid; in this work, 50 evenly spaced angles spanning 2p radians were used. By encompassing 95% of the pixels from the control rats, this ellipsoid thus defines the boundaries of a region of S0 and T2 values that represent "normal" lung tissue with ≧95% confidence.

To eliminate data points from dosed animals that were within the ellipsoid (i.e. "normal" pixels), the ellipsoid was first mapped to a unit circle centered at the origin by use of the transformation shown as equation A.5:

$$x' = -\dfrac{\overline{\ln(S_0)} - x}{r \times CD_{11}} \tag{A.5}$$

$$y' = -\dfrac{\overline{\ln(S_0)} + CD_{12} \times x - CD_{11} \times y}{r \times CD_{11} \times CD_{22}}$$

Eq. A.5 has been simplified to reflect the fact that CD21=0. Data points from dosed animals were also mapped using Eq. A.5, and any data points that met the condition:

$$S_0'^2 + T_2'^2 \leq 1 \tag{A.6}$$

fell within the unit circle and were therefore defined as "normal" and deleted.

Rat physiological data were analyzed using two-sample t-tests. The control data were compared to both the low dose and the high dose data using a confidence level $\alpha$=0.05; p-values below 0.05 were considered significant. Correlation coefficients and probabilities were calculated using a paired t-test.

Results: Table 1 shows the mean and median values of S0 and T2 from the segmented lung images of the control group.

TABLE 1

Mean (with standard deviation) and median values of $S_0$ (arb. units) and $T_2$ (ms) for the control animals at each time point. n = 5, except where noted.

|  | Pre Dose | Week 1 | Week 2† | Week 4 | Week 7 |
|---|---|---|---|---|---|
| $S_0$ Mean (SD) | 7.43 (1.60) | 7.34 (1.09)* | 7.01 (1.06)* | 6.55 (0.96)* | 6.70 (0.85)* |
| $S_0$ Median | 7.03 | 7.10 | 6.81 | 6.36 | 6.55 |
| $T_2$ Mean (SD) | 16.1 (3.8) | 15.6 (3.6)* | 15.2 (4.0)* | 14.4 (3.3)* | 13.4 (2.7)* |
| $T_2$ Median | 15.4 | 15.0 | 14.4 | 13.8 | 13.0 |

*p < 0.0001 compared to pre-dose values
†n = 4

Over the 7 weeks of the experiment, the average values (and standard deviations) of both S0 and T2 for the control animals generally decreased; thus, the S0 -T2 ellipsoids tended to shift slightly down and to the left while shrinking in size. Therefore, dosed animals were compared only to age-matched controls at each time point, and not to themselves at the pre-dose time point (i.e. animals did not act as their own controls in spite of the pre-dose data that were collected).

The fraction of "abnormal" pixels was calculated from the segmented lung images for each rat at each time point; results are shown in FIG. 7. Several LD rats had a strong initial response, but the percentage of "abnormal" pixels declined rapidly to the 5% level (as shown in the dashed line in FIG. 7), which is defined herein as "normal". By week 4 the LD rats were essentially indistinguishable from the control rats. By comparison, the HD rats generally showed a stronger response (i.e. greater fraction of "abnormal" pixels) throughout the duration of the experiment, with the percentage of "abnormal" pixels declining much less rapidly.

FIG. 8 shows the mean S0 and T2 values for the "abnormal" pixels of all the dose rats at each time point, along with the mean values for the controls (not differentiated temporally). There is a strong correlation between T2 and S0 (r=0.93, p<0.001). Weeks 4 and 7 results from the LD group had a very small percentage of "abnormal" pixels (as shown in FIG. 7) and were therefore virtually indistinguishable from controls using MRI when all pixels were considered.

Physiological Measurements: FIG. 9 shows the mean body weights of the animals, measured immediately prior to each imaging session. Both dose groups lost a significant amount of weight the first week, but by the end of the experiments all groups were essentially the same. Other than the initial weight loss, no other outward signs of distress were observed.

FIG. 10 shows mean week 7 results of: right lung water content measured gravimetrically, in grams (A); right lung collagen content from hydroxyproline measurement, in percentage of dry lung weight (B); left lung collagen content, in percentage of blue-stained pixels in the histology images (C); percentage of the whole lung found to be "abnormal" by in vivo MRI (D); and in vivo QCC (E).

Correlation of MRI with Post-mortem Results: In Table 2, mean T2 and S0 values for normal lungs and "abnormal" pixels in both dose groups are compared to determine how well these MRI parameters correlate with disease-induced changes in collagen content (as measured by hydroxyproline).

TABLE 2

Correlation coefficients (r) and p-values for correlating collagen content (by the hydroxyproline method) and water weight of the different dose groups with mean $S_0$, $T_2$, and $S_0 \times T_2$.

|  | $S_0$ | $T_2$ | $S_0 \times T_2$ |
|---|---|---|---|
| HD, collagen | r = 0.79<br>p = 0.11 | r = 0.64<br>p = 0.24 | r = 0.98<br>p = 0.004 |
| HD, water | r = 0.88<br>p = 0.05 | r = 0.51<br>p = 0.38 | r = 0.91<br>p = 0.03 |
| LD, collagen | r = 0.31<br>p = 0.61 | r = 0.33<br>p = 0.58 | r = 0.69<br>p = 0.19 |
| LD, water | r = −0.56<br>p = 0.32 | r = 0.82<br>p = 0.09 | r = 0.64<br>p = 0.24 |
| Control, collagen | r = −0.21<br>p = 0.72 | r = 0.69<br>p = 0.19 | r = −0.53<br>p = 0.35 |
| Control, water | r = −0.72<br>p = 0.16 | r = 0.65<br>p = 0.23 | r = −0.56<br>p = 0.33 |

A p-value of <0.05 is significant.

This assumes that the bulk of the collagen resided in "abnormal" regions, which may only be true for the HD rats. The mean T2 and S0 values of all pixels were correlated with water content (measured gravimetrically), since water signal is contributed from the entire lung. Of the correlation tests, the only significant correlations were found for the HD rats between S0×T2 and collagen (r=0.98, p=0.004), and between S0×T2 and water (r=0.91, p=0.03). No significant correlations were found for S0 or T2 alone. There were no significant correlations with collagen when considering all pixels from the dose groups (data not shown), as opposed to only the "abnormal" pixels.

As demonstrated by these experiments, proton MRI approaches for lung visualization may have several applications. In a clinical setting, they may be useful for long-term patient monitoring to evaluate changes in disease or treatment efficacy. Pre-clinical uses may include: animal screening to prevent blind sacrifice, pharmaceutical testing, facilitating targeted tissue harvesting, and monitoring of disease progression and resolution. Indeed, an example of the pre-clinical utility was realized during this study. When the LD group was seen to have a weaker than expected response, the HD group was added mid-study at minimal cost and inconvenience.

In conclusion, these experiments have shown that bivariate statistical analysis of S0 and T2 acquired using MRI is sensitive to inflammation and fibrotic changes in the lung. They have also shown that the MRI results are able to distinguish diseased lungs as effectively as post-mortem measurements while providing locally sensitive information and allowing for time-course measurements.

While the invention has been illustrated and described in detail in the drawings and foregoing description, the same is to be considered as illustrative and not restrictive in character. Only certain embodiments have been shown and described, and all changes, equivalents, and modifications that come within the spirit of the invention described herein are desired to be protected. Any experiments, experimental examples, or experimental results provided herein are intended to be illustrative of the present invention and should not be considered limiting or restrictive with regard to the invention scope. Further, any theory, mechanism of operation, proof, or finding stated herein is meant to further enhance understanding of the present invention and is not intended to limit the present invention in any way to such theory, mechanism of operation, proof, or finding.

Thus, the specifics of this description and the attached drawings should not be interpreted to limit the scope of this invention to the specifics thereof. Rather, the scope of this invention should be evaluated with reference to the claims appended hereto. In reading the claims it is intended that when words such as "a", "an", "at least one", and "at least a portion" are used there is no intention to limit the claims to only one item unless specifically stated to the contrary in the claims. Further, when the language "at least a portion" and/or "a portion" is used, the claims may include a portion and/or the entire items unless specifically stated to the contrary. Likewise, where the term "input" or "output" is used in connection with an electric device or fluid processing unit, it should be understood to comprehend singular or plural and one or more signal channels or fluid lines as appropriate in the context. Finally, all publications, patents, and patent applications cited in this specification are herein incorporated by reference to the extent not inconsistent with the present disclosure as if each were specifically and individually indicated to be incorporated by reference and set forth in its entirety herein.

We claim:

1. A method for detecting the presence of abnormal tissues using magnetic resonance imaging comprising the steps of:
   a. selecting at least two parameters detectable by magnetic resonance imaging,
   b. generating a first set of measured data points from at least one baseline tissue by measuring the selected parameters at a first set of data points in the baseline tissue using magnetic resonance imaging,
   c. determining a confidence region using the measured data points,
   d. generating a second set of measured data points from a second tissue by measuring the selected parameters at a second set of data points in the second tissue using magnetic resonance imaging,
   e. identifying the data points from the second set of measured data points that do not fall within the confidence region.

2. The method of claim 1 wherein measurements of the selected parameters from portions of the magnetic resonance image outside of the first set of data points are ignored during the step of generating the confidence region.

3. The method of claim 1 wherein measurements of the selected parameters from portions of the magnetic resonance image outside of the second set of data points are ignored during the step of identifying the data points from the second set of measured data points that do not fall within the confidence region.

4. The method of claim 1 comprising the additional step of highlighting the data points from the second set of measured data points that do not fall within the confidence region onto their location in an image of the second tissue.

5. The method of claim 1 comprising the additional step of generating an image of the second tissue wherein the image delineates the location of the data points from the second set of measured data points that do not fall within the confidence region.

6. The method of claim 1 wherein the parameters are selected from t1, t2, t2*, signal intensity, diffusion, and combinations thereof.

7. The method of claim 6 wherein the parameters are t2 and signal intensity.

8. The method of claim 1 wherein the step of generating the confidence region is performed using a probability based confidence interval calculation.

9. The method of claim 8 wherein the step of generating the confidence region is performed using a multivariate analysis.

10. The method of claim 9 wherein the step of generating the confidence region is performed using a bivariate analysis.

11. An apparatus for detecting the presence of abnormal tissues comprising:
   a. a magnetic resonance imaging system in communication with
   b. a computer wherein,
   c. the apparatus is configured to detect at least two parameters at a set of data points in at least one first tissue sample by making a magnetic resonance image of at least one first tissue sample,
   d. the apparatus is configured to detect at least two parameters at a set of data points in a second tissue sample by making a magnetic resonance image of a second tissue sample,
   e. the apparatus is configured to generate a set of measured data points for each tissue sample for each of the selected parameters,
   f. the apparatus is configured to calculate a confidence region using the measured data points from at least one first tissue sample, and
   g. the apparatus is configured to identify data points from at least one second tissue sample that do not fall within the calculated confidence region.

12. The apparatus of claim 11 further configured to ignore measurements of the selected parameters from portions of the magnetic resonance image outside of the set of data points prior to calculating the confidence region.

13. The apparatus of claim 11 further configured to ignore measurements of the selected parameters from portions of the magnetic resonance image outside of the second set of data points prior to identifying data points that do not fall within the calculated confidence region.

14. The apparatus of claim 11 further configured to highlight the data points from the second set of measured data points that do not fall within the confidence region onto their location in an image of the second tissue sample.

15. The apparatus of claim 11 further configured to generate an image of a second tissue wherein the image delineates the location of the data points from the second set of measured data points that do not fall within the confidence region.

16. The apparatus of claim 11 wherein at least two parameters are selected from t1, t2, t2*, signal intensity, diffusion, and combinations thereof.

17. The apparatus of claim 11 wherein the two parameters are t2 and signal intensity.

18. The apparatus of claim 11 further configured to calculate the confidence region using a probability based confidence interval calculation.

19. The apparatus of claim 18 further configured to calculate the confidence region using a multivariate analysis.

20. The apparatus of claim 19 further configured to calculate the confidence region using a bivariate analysis.

21. The method of claim 1, wherein the baseline tissue does not have an anomaly that is suspected to exist in the second tissue.

22. The method of claim 1, wherein the baseline tissue is healthy tissue.

\* \* \* \* \*